US010002227B2

(12) United States Patent
Netravali et al.

(10) Patent No.: US 10,002,227 B2
(45) Date of Patent: Jun. 19, 2018

(54) SYSTEM AND METHOD FOR REGISTRATION IN ORTHOPAEDIC APPLICATIONS

(71) Applicant: CUREXO TECHNOLOGY CORPORATION, Fremont, CA (US)

(72) Inventors: Nathan A. Netravali, Palo Alto, CA (US); In K. Mun, Nanuet, NY (US); Li Lu, Sunnyvale, CA (US)

(73) Assignee: THINK SURGICAL, INC., Fremont, CA (US)

( * ) Notice: Subject to any disclaimer, the term of this patent is extended or adjusted under 35 U.S.C. 154(b) by 489 days.

(21) Appl. No.: 14/429,301

(22) PCT Filed: Oct. 15, 2013

(86) PCT No.: PCT/IB2013/002311
§ 371 (c)(1),
(2) Date: Mar. 18, 2015

(87) PCT Pub. No.: WO2014/045119
PCT Pub. Date: Mar. 27, 2014

(65) Prior Publication Data
US 2015/0220682 A1 Aug. 6, 2015

Related U.S. Application Data

(60) Provisional application No. 61/702,529, filed on Sep. 18, 2012, provisional application No. 61/702,561, (Continued)

(51) Int. Cl.
*A61B 34/10* (2016.01)
*G06F 19/12* (2011.01)
(Continued)

(52) U.S. Cl.
CPC .............. *G06F 19/12* (2013.01); *A61B 17/15* (2013.01); *A61B 34/10* (2016.02); *G06T 17/00* (2013.01);
(Continued)

(58) Field of Classification Search
CPC ...................................................... A61B 34/10
See application file for complete search history.

(56) References Cited

U.S. PATENT DOCUMENTS 5,156,777 A 10/1992 Kaye
5,682,886 A 11/1997 Delp et al.
(Continued)

FOREIGN PATENT DOCUMENTS

WO 2011034434 A1 3/2011

OTHER PUBLICATIONS

International Search Report dated Apr. 10, 2014 for International Application No. PCT/IB2013/002311 filed Oct. 15, 2013.
(Continued)

*Primary Examiner* — Zade Coley
*Assistant Examiner* — Olivia C Chang
(74) *Attorney, Agent, or Firm* — Avery N. Goldstein; Blue Filament Law, PLLC

(57) ABSTRACT

Described herein are systems and methods for creating a custom registration guide. In general, the methods may include receiving scan data of a patient's bone; creating instructions based on the scan data for creating a three-dimensional surface model of the patient's bone; and moving a plurality of moveable elements, coupled to the adjustable model, based on the instructions. The method may further include the steps of placing a malleable registration guide onto the adjustable model and shaping the registration guide to fit to the adjustable model. The method may further include the step of intraoperatively determining the location (Continued)

of a patient's bone using the custom registration guide. The step of determining the location of the patient's bone may include the steps of coupling the registration guide and fiducial markers to the patient's bone.

4 Claims, 14 Drawing Sheets

Related U.S. Application Data filed on Sep. 18, 2012, provisional application No. 61/716,389, filed on Oct. 19, 2012.

(51) Int. Cl.
*G06T 17/00* (2006.01)
*A61B 17/15* (2006.01)
*A61B 6/03* (2006.01)
*A61B 6/00* (2006.01)
*A61B 17/00* (2006.01)
*A61B 34/20* (2016.01)
*A61B 90/00* (2016.01)

(52) U.S. Cl.
CPC ............ *A61B 6/032* (2013.01); *A61B 6/505* (2013.01); *A61B 2017/00526* (2013.01); *A61B 2034/105* (2016.02); *A61B 2034/108* (2016.02); *A61B 2034/2051* (2016.02); *A61B 2034/2055* (2016.02); *A61B 2090/363* (2016.02); *A61B 2090/3983* (2016.02); *G05B 2219/49025* (2013.01); *G06T 2200/08* (2013.01); *G06T 2210/41* (2013.01)

(56) References Cited

U.S. PATENT DOCUMENTS

| | | |
|---|---|---|
| 5,871,018 A | 2/1999 | Delp et al. |
| 6,074,394 A | 6/2000 | Krause |
| 6,241,735 B1 | 6/2001 | Marmulla |
| 6,385,475 B1 | 5/2002 | Cinquin et al. |
| 7,785,330 B2 | 8/2010 | Sherman et al. |
| 8,118,815 B2 | 2/2012 | van der Walt |
| 8,126,533 B2 | 2/2012 | Lavallee |
| 8,270,253 B1 | 9/2012 | Roche et al. |
| 8,303,596 B2 | 11/2012 | Plaβky et al. |
| 2003/0216669 A1* | 11/2003 | Lang ................ A61B 5/4528 600/587 |
| 2005/0182320 A1 | 8/2005 | Stifter et al. |
| 2008/0154127 A1 | 6/2008 | Disilvestro et al. |
| 2009/0270868 A1 | 10/2009 | Park et al. |
| 2011/0218545 A1 | 9/2011 | Catanzarite et al. |
| 2011/0257653 A1 | 10/2011 | Hughes et al. |
| 2012/0116203 A1 | 5/2012 | Vancraen et al. |
| 2012/0316567 A1 | 12/2012 | Gross et al. |
| 2013/0144392 A1 | 6/2013 | Hughes |

OTHER PUBLICATIONS

Supplementary Partial European Search Report dated Apr. 6, 2017 for European Application No. 13839148 filed Oct. 15, 2013.

\* cited by examiner

200

S210: place a malleable registration guide onto an adjustable model

S220: shape the registration guide to fit to the adjustable model

S230: couple the shaped registration guide and fiducial markers to the patient's bone S240: immobilize the registration guide with respect to the bone

300

S310: determine intraoperatively the location of the fiducial markers

S320: determine the location of the registration guide with respect to the fiducial markers S330: determine the location of the patient's bone with respect to the registration guide S340: perform a surgical procedure on the patient's bone

SYSTEM AND METHOD FOR REGISTRATION IN ORTHOPAEDIC APPLICATIONS

CROSS-REFERENCE TO RELATED APPLICATIONS

This application claims priority of U.S. Provisional Patent Application Ser. No. 61/702,529 filed Sep. 18, 2012 entitled "A METHOD USING AN ADJUSTABLE JIG FOR REGISTRATION IN ORTHOPAEDIC APPLICATIONS"; U.S. Provisional Patent Application Ser. No. 61/702,561 filed Sep. 18, 2012 entitled "A NOVEL METHOD FOR REGISTRATION IN ORTHOPAEDIC APPLICATIONS"; and U.S. Provisional Application Ser. No. 61/716,389 filed Oct. 19, 2012 entitled "SYSTEM AND METHOD FOR REGISTRATION IN ORTHOPAEDIC APPLICATIONS", the entire contents of each is incorporated herein by reference in its entirety.

FIELD OF THE INVENTION

This invention relates generally to the bone registration field, and more specifically to a new and useful system and method for spatially registering bone in three-dimensional space, as well as using adjustable jigs and customized patient specific jigs for orthopaedic applications.

BACKGROUND OF THE INVENTION

Throughout a lifetime, bones and joints become damaged and worn through normal use and traumatic events. This degradation of the joints involving the articular cartilage and subchondral bone is known as arthritis and results in symptoms including joint pain, tenderness, stiffness, and potential locking of the joint.

Joint replacement arthroplasty is an orthopedic procedure in which the arthritic surface of the joint is replaced with a prosthetic component. It is considered the primary form of treatment to relieve joint pain or dysfunction that may limit mobility. During an arthroplasty procedure, the ends of the bone and articular cartilage are resurfaced (i.e., by cutting the bone) to match the backside of the implant.

The accurate placement and alignment of an implant is a large factor in determining the success of a joint arthroplasty procedure. A slight misalignment may result in poor wear characteristics, reduced functionality, and a decreased longevity.

In order to achieve accurate implant placement and alignment, one must accurately position the cutting tool vis-à-vis the bone prior to making any bone cuts. In some methods, a cutting jig may be used to accurately position and orient a cutting tool such as a saw, drill, or reamer. In other methods, the cuts may be made using a surgical assist device (e.g., a surgical robot) that controls a saw, cutter, or reamer. When a surgical assist device is used to make the cuts, the bone's position and orientation must be known precisely in three-dimensional space (and hence vis-à-vis the surgical assist device) to ensure that the cuts are made in the correct location. The current available methods of determining spatial orientation and location of a bone consist of registering the bones in a three-dimensional space, either using previously placed fiducial markers or by collecting or digitizing the locations of several points on the surface of the bone. The process using previously placed fiducial markers requires an additional surgical operation, and the process of digitizing points on the surface of the bone can be time consuming.

Thus, there is a need for a more efficient method for a surgeon to rapidly and accurately determine the spatial orientation and location of a bone during orthopedic surgery. This invention provides such a new and useful system and method.

SUMMARY OF THE INVENTION

A system and method is provided for a surgeon to rapidly and accurately determine the spatial orientation and location of a bone during orthopedic surgery. An embodiment of the inventive method for creating a three-dimensional model of a patient's bone includes the steps of receiving scan data of a patient's bone and creating instructions based on the scan data for creating a three-dimensional surface model of the patient's bone, and moving a plurality of moveable elements, coupled to an adjustable model, based on the instructions, and then locking the movable elements into position.

A method for creating a custom registration guide based on a three-dimensional model of a patient's bone is also provided, and includes the steps of placing a malleable registration guide onto an adjustable model, and shaping the registration guide to fit to the adjustable model, and subsequently coupling the shaped registration guide and a set of fiducial markers to the patient's bone.

A method for intraoperatively determining the location of a patient's bone is also provided, and includes the steps of determining intraoperatively the location of fiducial markers coupled to the patient's bone and/or to a registration guide, determining the location of the registration guide with respect to the fiducial markers, and determining the location of the patient's bone with respect to the registration guide.

A system for creating a three-dimensional model of a patient's bone is provided, the system including a processor configured to receive patient scan data and to transform the patient scan data into adjustable model instructions, and a machine, coupled to an adjustable model having a plurality of moveable elements, configured to receive the adjustable model instructions and to move a number of the moveable elements. The processor is further configured to transform the patient scan data into a three-dimensional virtual model and create the adjustable model instructions based on the three-dimensional virtual model. A malleable registration guide blank is configured to couple to the adjustable model and to be shaped to fit the adjustable model to form a shaped custom registration guide that is configured to fit to the patient's bone in a unique way.

A system for intraoperatively determining the location of a patient's bone is also provided, the system including a digitizer configured to determine intraoperatively the location of the fiducial markers, and a processor, coupled to the digitizer, and configured to determine the location of the registration guide with respect to the fiducial markers and to determine the location of the patient's bone with respect to the registration guide.

Preoperative surgical planning software and an adjustable registration jig for determining three-dimensional spatial orientation of a bone during a joint arthroplasty procedure is also provided. Embodiments of the inventive registration jig may be used for any orthopaedic surgeries in which bone cuts are made. The inventive surgical planning software creates a three-dimensional model of the bone based on medical imaging including CT, MRI, or X-ray scans and optimizes the location and settings of the registration jig to uniquely fit the anatomical surface of the bone. The registration jig is designed to generally fit the bone anatomy of interest but has adjustable settings such that it can be fixed on to the surface of the bone in a unique manner. The surgical planning software determines how to adjust the settings on the registration jig such that the position of the jig relative to the surface of the bone is known in six degrees of freedom. Embodiments of the registration jig are equipped with fiducial markers that can be optical, mechanical, or electro-magnetic. The fiducial markers may be a part of the registration jig or they may be separate modular pieces that attach to the registration jig in a specific location or that attach to the bone directly through an opening in the registration jig. The fiducial markers, whose positions relative to the registration jig are known and whose positions relative to the patient bone will be known once the registration jig is placed on the bone in its unique position with known settings, can then be rapidly located intraoperatively to determine the spatial orientation of the bone in three-dimensions. In embodiments the registration jig and/or fiducial markers may or may not be removed from the patient bone prior to cutting of the bone surface.

A three-dimensional registration jig (guide) that mates with the contours of a surface of a patient bone is provided. The registration jig may be used for any orthopaedic surgeries in which bone cuts are made. The surgical planning software creates a three-dimensional model of the bone based on medical imaging including CT, MRI, or X-ray scans and creates the plan for a three-dimensional registration jig to uniquely match the anatomical surface of the bone. The registration jig consists of an anatomy-specific inner surface that mates with the bone surface in a unique manner and an external surface consisting of fiducial markers that can be optical, mechanical, or electro-magnetic. The fiducial markers may be a part of the registration guide or they may be separate modular pieces that attach to the registration guide in a specific location or that attach directly to the bone through an opening in the registration guide. The fiducial markers, whose positions relative to the registration guide are known and whose positions relative to the patient bone will be known once the registration guide is placed on the bone in its unique position, can then be rapidly located intraoperatively to determine the spatial orientation of the bone in three-dimensions. The registration guide and/or fiducial markers may or may not be removed from the patient bone prior to cutting of the bone surface.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 3 is a flowchart depicting a method for intraoperatively determining the location of a patient's bone according to an embodiment of the invention;

FIGS. 12A-12C are skeletal representations of the proximal human tibia from various perspectives demonstrating how the registration jig (guide) would fit on the bone according to embodiments of the invention;

DESCRIPTION OF THE INVENTION

Figure 1:
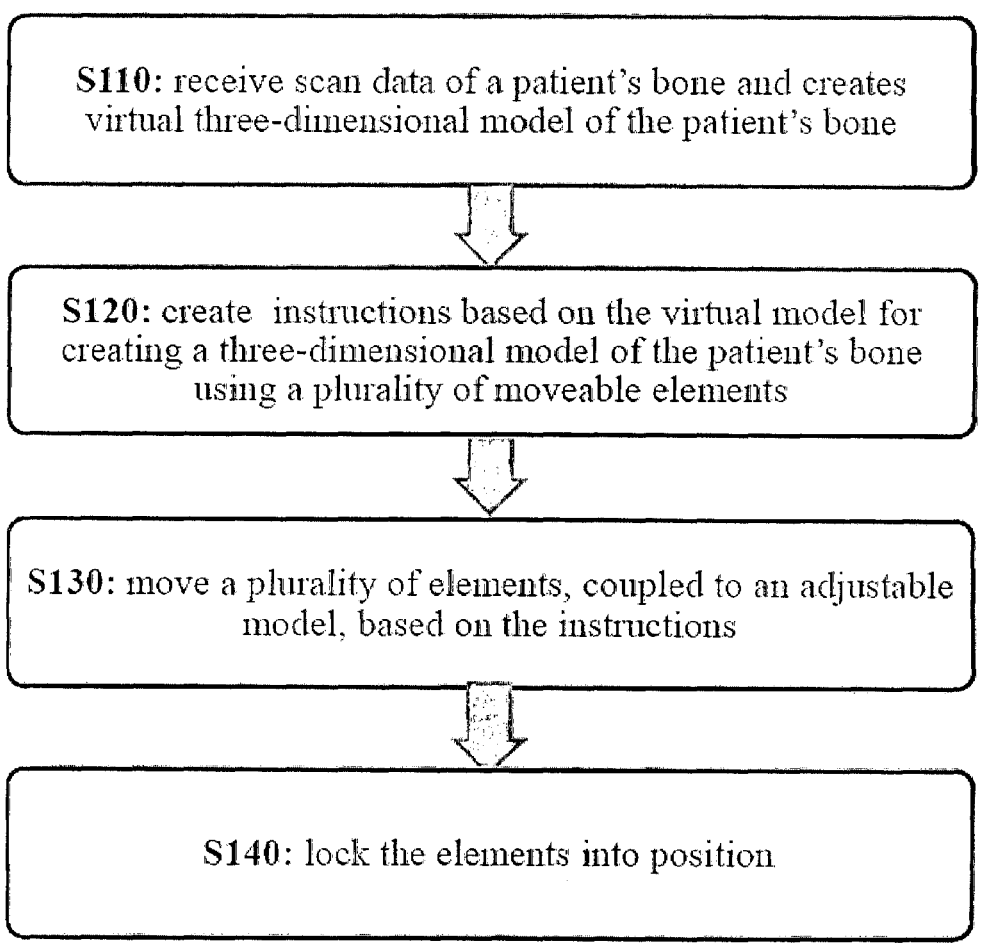
FIG. 1 is a flowchart depicting a method for creating a three-dimensional model of a patient's bone according to an embodiment of the invention.

The present invention has utility as custom registration jigs (guides), and systems and methods for producing such registration guides. The custom registration jigs (guides) are customized in three-dimensional space to fit specific bone surfaces of specific patients.

Preoperative surgical planning software and an adjustable registration jig for determining three-dimensional spatial orientation of a bone during a joint arthroplasty procedure is also provided. Embodiments of the inventive registration jig may be used for any orthopaedic surgeries in which bone cuts are made. The inventive surgical planning software creates a three-dimensional model of the bone based on medical imaging including CT, MRI, or X-ray scans and optimizes the location and settings of the registration jig to uniquely fit the anatomical surface of the bone. The registration jig is designed to generally fit the bone anatomy of interest but has adjustable settings such that it can be fixed on to the surface of the bone in a unique manner. The surgical planning software determines how to adjust the settings on the registration jig such that the position of the jig relative to the surface of the bone is known in six degrees of freedom. Embodiments of the registration jig are equipped with fiducial markers that can be optical, mechanical, or electro-magnetic. The fiducial markers may be a part of the registration jig or they may be separate modular pieces that attach to the registration jig in a specific location or that attach to the bone directly through an opening in the registration jig. The fiducial markers, whose positions relative to the registration jig are known and whose positions relative to the patient bone will be known once the registration jig is placed on the bone in its unique position with known settings, can then be rapidly located intraoperatively to determine the spatial orientation of the bone in three-dimensions. In embodiments the registration jig and/or fiducial markers may or may not be removed from the patient bone prior to cutting of the bone surface.

A three-dimensional registration jig (guide) that mates with the contours of a surface of a patient bone is provided. The registration jig may be used for any orthopaedic surgeries in which bone cuts are made. The surgical planning software creates a three-dimensional model of the bone based on medical imaging including CT, MRI, or X-ray scans and creates the plan for a three-dimensional registration jig to uniquely match the anatomical surface of the bone. The registration jig consists of an anatomy-specific inner surface that mates with the bone surface in a unique manner and an external surface consisting of fiducial markers that can be optical, mechanical, or electro-magnetic. The fiducial markers may be a part of the registration guide or they may be separate modular pieces that attach to the registration guide in a specific location or that attach directly to the bone through an opening in the registration guide. The fiducial markers, whose positions relative to the registration guide are known and whose positions relative to the patient bone will be known once the registration guide is placed on the bone in its unique position, can then be rapidly located intraoperatively to determine the spatial orientation of the bone in three-dimensions. The registration guide and/or fiducial markers may or may not be removed from the patient bone prior to cutting of the bone surface.

An adjustable registration jig and systems for fitting such registration jigs to a bone using a preoperative planning software is provided. Embodiments of the registration jigs are adjustable such that they can be placed on the bone surfaces of specific patients and the settings adjusted such that the registration jigs fit on the bone in a unique manner. Embodiments of the preoperative planning software determine the settings for the adjustable jig such that the jig fits precisely on the bone. Embodiments of the preoperative planning software use medical images including CT, MRI, or X-ray scans of patients bones as input. The scan data can be used to create a three-dimensional model of the bone(s) involved in the procedure using the preoperative planning software.

In a specific embodiment, each bone has a generic adjustable jig that can be placed on the bone and secured to its surface by adjusting some settings. The settings on these generic adjustable jigs can be changed to accommodate bones of a variety of sizes. The jigs can be made from polymer, ceramic, metal, or other suitable material, and sterilized. The preoperative planning software then determines the appropriate settings for the registration jig such that the jig will securely mate with the bone surface. Embodiments of the adjustable jigs have three or more fiducial markers that can be optical, mechanical, or electro-magnetic. The fiducial markers may be a part of the registration jig or they may be separate modular pieces that attach to the registration jig in a specific location, or that attach directly to the bone through an opening in the jig. The fiducial markers, whose positions relative to the registration jig are known and whose positions relative to the patient bone will be known once the registration jig is placed on the bone and adjusted to its unique position, can then be rapidly located intraoperatively to determine the spatial orientation of the bone in three-dimensions.

In another embodiment, the preoperative planning software generates a three-dimensional model of an adjustable jig that consists of multiple pieces that mate with the surface of the bone. As will be shown with respect to FIG. 9, the jigs multiple pieces attach to each other using an adjustable mechanism, such as a rail. The preoperative planning software determines the appropriate settings for the registration jig such that the jig will securely mate with the bone surface. In this embodiment, the registration jig fits on the surface of the bone in a unique manner making use of the specific anatomy of the patient that may include distinguishing features such as worn bone surfaces or osteophytes. The software can determine three or more specific points on the registration jig that can be used to rapidly determine the spatial location and orientation of the adjustable jig. These specific registration points can serve as locations for fiducial markers that can be optical, mechanical, or electro-magnetic. The fiducial markers may be a part of the registration jig or they may be separate modular pieces that attach to the registration jig in a specific location or that attach directly to the bone through an opening in the jig. The fiducial markers, whose positions relative to the registration jig are known and whose positions relative to the patient bone will be known once the registration jig is placed on the bone in its unique position, can then be rapidly located intraoperatively to determine the spatial orientation of the bone in three-dimensions.

In certain embodiments, the preoperative planning software generates instructions for computer-controlled tool paths to machine the patient-specific registration jigs in a tool path data file. The tool path can be provided as input to a CNC mill or other automated machining or rapid prototyping system, and the registration jigs can be machined from polymer, ceramic, metal, or other suitable material, and sterilized. The customized patient specific jigs are spatially registered to the bone surface in three-dimensional space The parts of the registration jig can be made of varying thickness, but shall be made of a minimum thickness such that the guide can maintain its structural stiffness without deformation. Certain areas of the jig can be made thicker to provide this structural rigidity.

During surgery, once the registration jig is applied to the bone intraoperatively, the jig can be adjusted such that it fits on the bone securely in a unique manner. The jig can be secured to the bone using fixation pins, fasteners, or another method of immobilizing the jig with respect to the bone. The fixation pins may or may not also serve as the fiducial markers. Once the location of the fiducial markers has been determined using a digitizer or other digital location device, the location and orientation of the underlying bone can be determined as there is a unique relationship between the orientation and location of the registration jig and that of the bone when the settings on the registration jig are adjusted according to the preoperative planning software. Prior to beginning the bone cutting, the registration jig may or may not be removed from the bone surface. If the registration jig is removed from the surface of the bone, the fiducial markers preferably remain attached to the bone during bone cutting. These fiducial markers can be used at any point during the surgery to rapidly determine the location and orientation of the bone.

The registration jig may be modular in nature, consisting of multiple pieces. Once the registration jig is adjusted and is secured to the bone, part of the registration jig can be removed from the bone, leaving part of the jig fixed to the bone. The portion of the registration jig that remains fixed to the bone should contain on or within it, fiducial markers that may be used to determine the location and orientation of the registration jig. Once the location and orientation of these fiducial markers is known, the original location of the registration jig can be determined and the location and orientation of the underlying bone can be determined as there is a unique mating between the bone and the registration jig.

Embodiments of the inventive registration jig or guide can be customized to fit the contours of an individual patient bone surface. Depending on the embodiment, the registration guides are automatically planned and generated. The preoperative planning software uses medical images including CT, MRI, or X-ray scans of patients' bones as input. The scan data can be used to create a three-dimensional model of the bone(s) involved in the procedure using the preoperative planning software. The software then generates a three-dimensional model of a registration guide that mates with the surface of the bone. Based on the three-dimensional model, the software generates instructions for computer-controlled tool paths to machine the patient-specific registration guide in a tool path data file. The tool path can be provided as input to a CNC mill or other automated machining or rapid prototyping system, and the registration guides can be machined from polymer, ceramic, metal, or other suitable material, and sterilized. The registration guide can be made of varying thickness, but shall be made of a minimum thickness such that the guide can maintain a structural stiffness without deformation. Certain areas can be made thicker to provide this structural rigidity.

The generated registration guide fits on the surface of the bone in a unique manner making use of the specific anatomy of the patient that may include distinguishing features such as worn bone surfaces or osteophytes. The software can determine three or more specific points on the registration guide that can be used to rapidly determine the spatial location and orientation of the registration guide. These specific registration points can serve as locations for fiducial markers that can be optical, mechanical, or electro-magnetic. The fiducial markers may be a part of the registration guide or they may be separate modular pieces that attach to the registration guide in a specific location or that attach directly to the bone through an opening in the registration guide. The fiducial markers, whose positions relative to the registration guide are known, and whose positions relative to the patient bone will be known once the registration guide is placed on the bone in its unique position, can then be rapidly located intraoperatively to determine the spatial orientation of the bone in three-dimensions.

During surgery on the subject patient for which the customized guide was formed, once the registration guide is applied to the bone intraoperatively, the guide can be secured to the bone using fixation pins, fasteners, or another method of immobilizing the guide with respect to the bone. The fixation pins may or may not also serve as the fiducial markers. Once the location of the fiducial markers has been determined using a digitizer or other digital locating device, the location and orientation of the underlying bone can be determined as there is a unique mating between the registration guide and the bone. Prior to beginning the bone cutting, the registration guide may or may not be removed from the bone surface. If the registration guide is removed from the surface of the bone, the fiducial markers shall preferably remain attached to the bone during bone cutting. These fiducial markers can be used at any point during the surgery to rapidly determine the location and orientation of the bone.

In certain embodiment of the customized registration guide, the registration guide may be modular in nature, consisting of multiple pieces. Once the registration guide is secured to the bone, part of the registration guide can be removed from the bone, leaving part of the guide fixed to the bone. This part that remains fixed to the bone should contain on or within it, fiducial markers that may be used to determine the location and orientation of the registration guide. Once the location and orientation of these fiducial markers is known, the original location of the registration guide can be determined and the location and orientation of the underlying bone can be determined as there is a unique mating between the bone and the registration guide.

Referring now to the figures, FIG. 1 shows an inventive method 100 for creating a three-dimensional model of a patient's bone may include the steps of receiving scan data of a patient's bone in block S110; creating instructions based on the scan data for creating a three-dimensional surface model of the patient's bone in block S120; and moving a plurality of moveable elements, coupled to an adjustable model, based on the instructions in block S130. In certain embodiments of the inventive method, the creating of a three-dimensional model of a patient's bone may further include the step of creating a virtual three-dimensional model of the patient's bone. The step of creating instructions may then comprise creating instructions based on the virtual model for creating a three-dimensional surface model of the patient's bone. In some specific embodiments, the creating of a three-dimensional model of a patient's bone may further include the step of locking the moveable elements into position in block S140. The method 100 preferably functions to create instructions based on the scan data for creating a three-dimensional model of the patient's bone in sufficient detail that a custom registration guide may be shaped by the three-dimensional model. In some embodiments, the method 100 preferably functions to create features or other markers in the three-dimensional model that may be transferred to the registration guide to aid in the bone registration process. In some embodiments, the method 100 preferably functions to enable the fabrication or creation of the three-dimensional model locally, for example, at the bedside or within the hospital, rather than having to send out the patient information and receive the three-dimensional model from a third party, thus reducing time, cost, and potential for error. The inventive method 100 is preferably used for bone registration for orthopedic surgery, but may alternatively be used for any suitable applications, clinical or otherwise. The method 100 can be configured and/or adapted to function for any suitable type of registration of bones or other materials or objects needing spatial registration in three-dimensional space.

As shown in FIG. 1, the inventive method 100 may include block S110, which recites receiving scan data of a patient's bone. Block S110 preferably functions to receive an input of scan data of a patient's bone. The scan data may be in the form of CT, MRI, or X-ray scans of patients' bones. The scan data may be collected by the systems and methods described herein or may alternatively, be collected prior to the creation of the custom registration guide by systems and methods specific to imaging.

Figure 4:
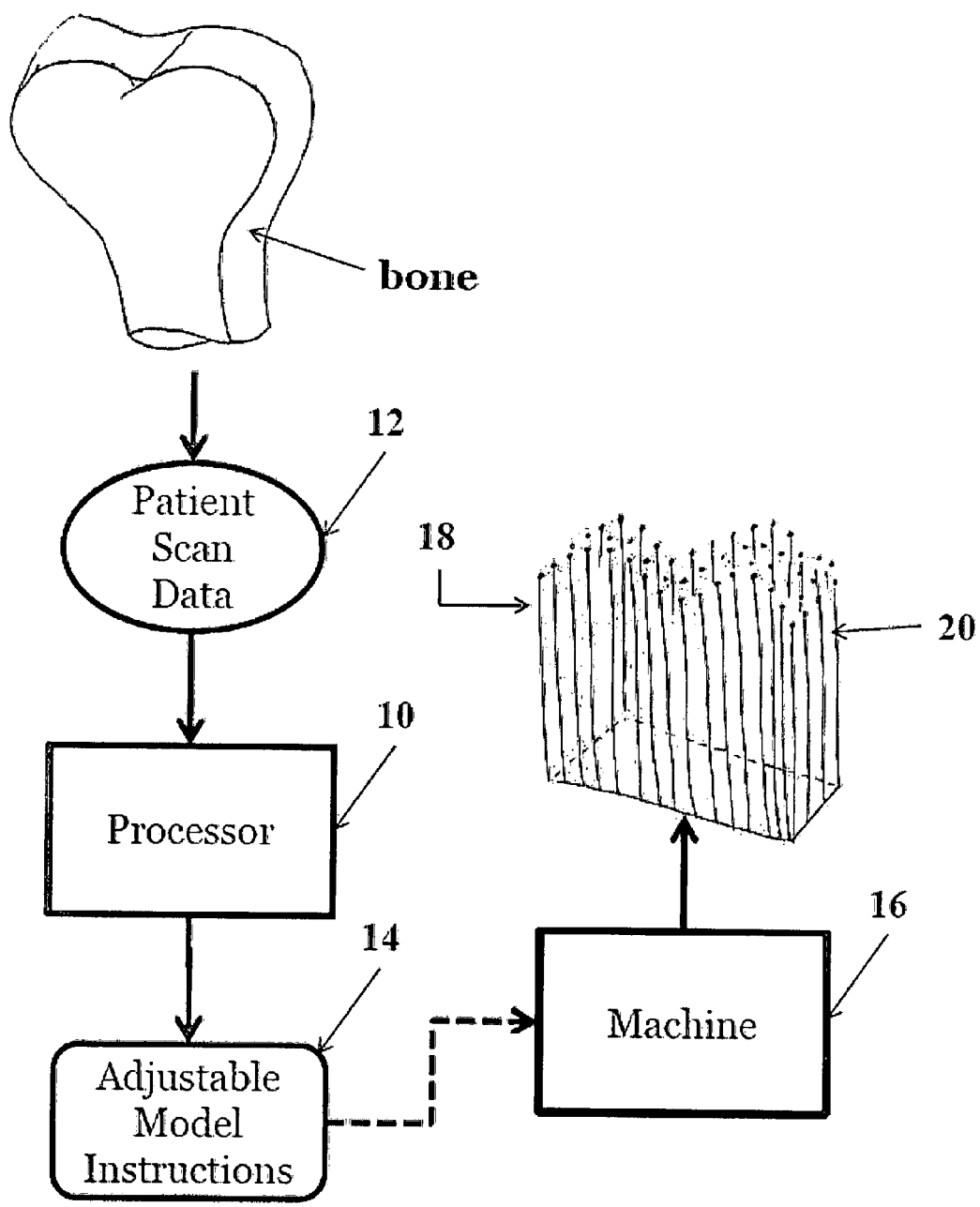
FIG. 4 is a schematic block diagram of a system for creating a three-dimensional model of a patient's bone according to an embodiment of the invention.

As shown in FIG. 1, the inventive method 100 may include block S120, which recites creating instructions based on the scan data for creating a three-dimensional surface model of the patient's bone. Block S120 preferably functions to create instructions for creating a model of the patient's bone using surgical preoperative surgical planning software. In some embodiments, the step of creating instructions may further include the step of creating a three-dimensional virtual software model of the patient's bone, and then creating the instructions based on the virtual three-dimensional software model. In some embodiments, the instructions are created to be machine readable. For example, the instructions may be received by machine 16, as shown in FIG. 4, which is coupled to the adjustable model 18. The instructions may be instructions for moving a plurality of elements and may be used to create the three-dimensional model using adjustable model 18. In some embodiments, the instructions are created such that the three dimensional model includes specific anatomy of the patient that may include distinguishing features such as worn bone surfaces or osteophytes. In some embodiments, the instructions are created such that the three dimensional model includes features that are not present in the patient's bone, but that can be used to rapidly determine the spatial location and orientation of the registration guide created using the three dimensional model. For example, the instructions may include directions to make holes or divots in specific locations. When the custom registration guide is shaped by the three-dimensional model, these specific registration points can serve as locations for fiducial markers that can be optical, mechanical, or electro-magnetic. The fiducial markers may be a part of the registration guide, or they may be separate modular pieces that attach in a specific location or through an opening in the guide. The fiducial markers, whose positions relative to the registration guide are known and whose positions relative to the patient bone will be known once the registration guide is placed on the bone in its unique position, can then be rapidly located intraoperatively to determine the spatial orientation of the bone in three-dimensions, as described in more detail below.

Figure 5:
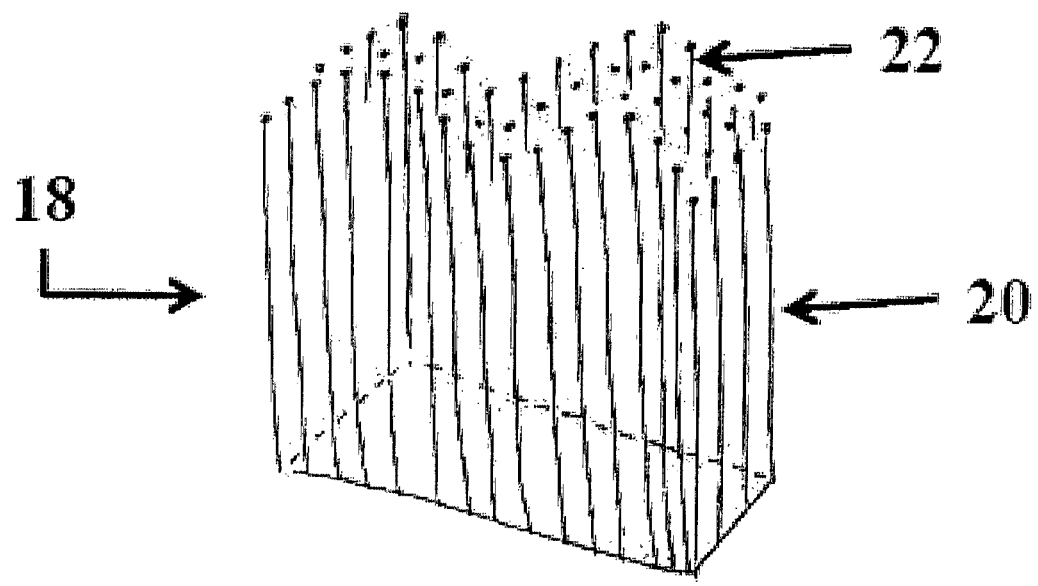
FIG. 5 illustrates an adjustable model having an adjustable outer surface and a plurality of moveable elements in accordance with embodiments of the invention.

As shown in FIG. 1, the method 100 may include block S130, which recites moving a plurality of moveable elements, coupled to an adjustable model, based on the instructions. Block S130 preferably functions to create a physical three-dimensional surface model of the patient's bone. In some embodiments, the physical three-dimensional model of the patient's bone may be created using an adjustable model 18, as shown in FIG. 5. As described in more detail below, the adjustable model 18 may include a plurality of moveable elements 20 that are configured to move into position such that the outer surface 22 of the model takes on the shape of the three-dimensional model of the patient's bone. The moveable elements are moved based on the instructions created in block S120.

For example, in one embodiment, the plurality of moveable elements may be a plurality of moveable pins. The proximal ends of the pins may be moved up or down such that the distal ends of the pins form an outer surface that takes on the desired shape of the three-dimensional model of the patient's bone. In certain embodiments, the resolution of the three-dimensional model may be determined by the number of pins, and/or the spacing between the pins. In certain embodiments, each pin may be directly adjacent to its neighboring pins such that there is essentially no space between the pins. In some embodiments, the distance from pin to pin (and/or the diameter of a pin) may be between 0 mm and 1 mm, while in certain embodiments, the distance from pin to pin (and/or the diameter of a pin) may be between 0 mm and 2.5 mm. In specific embodiments, the distance from pin to pin (and/or the diameter of a pin) may be between 0 mm and 5 mm. The spacing and sizing of the pins is preferably configured to enable a high resolution of the three dimensional model such that the detailed model may enable the creation of a detailed registration guide that uniquely couples to the patient's bone.

As described above, in certain embodiments, the instructions are created to be machine readable. For example, the instructions may be received by machine 16, as shown in FIG. 4, which is coupled to the adjustable model 18. The machine may move each of the individual pins based on the received instructions. Alternatively, the pins may be moved manually based on the instructions created.

As shown in FIG. 1, the method 100 may further include block S130, which recites locking the moveable elements into position in block S140. Block S140 preferably functions to fix the shape of the adjustable model such that it can be used to shape a custom registration guide. In some embodiments, once the moveable elements are moved into position, and the three dimensional surface model has been created, the moveable elements may then be locked into position. In some embodiments, machine 16 may further function to lock the moveable elements into position. Alternatively, the adjustable model 18 may further include a locking mechanism to fix the moveable elements into position.

Figure 2:
FIG. 2 is a flowchart depicting a method for creating a custom registration guide according to an embodiment of the invention.
Figure 2:
Figure 2:

As shown in FIG. 2, a method for creating a custom registration guide may include the steps of placing a malleable registration guide onto an adjustable model in block S210; shaping the registration guide to fit to the adjustable model in block S220; coupling the shaped registration guide and fiducial markers to the patient's bone in block S230; and immobilizing the registration guide with respect to the bone in block S240. The method preferably functions to create a custom registration guide that fits to the patient's bone in a unique way. In some embodiments, the method preferably functions to enable the fabrication or creation of the custom registration guide locally, for example, at the bedside or within the hospital, rather than having to send out the patient information and receive the custom registration guide from a third party, thus reducing time, cost, and potential for error. In some embodiments, the method preferably functions to enable the fabrication or creation of the custom registration guide manually and/or requiring a minimal use of tools. The preferred method is preferably used for bone registration for orthopedic surgery, but may alternatively be used for any suitable applications, clinical or otherwise. The method can be configured and/or adapted to function for any suitable type of registration of bones or other materials or objects needing spatial registration in three-dimensional space.

Figure 6:
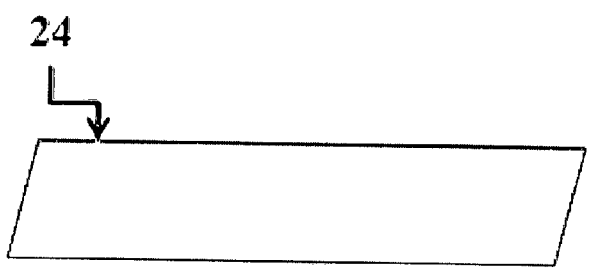
FIG. 6 illustrates a malleable registration guide blank in accordance with embodiments of the invention.

As shown in FIG. 2, the method 200 may include blocks S210 and S220, which recite placing a malleable registration guide blank onto an adjustable model and shaping the registration guide to fit to the adjustable model. Blocks S210 and S220 preferably function to couple a malleable registration guide blank (as shown in FIG. 6 for example) to the adjustable model, and to shape the malleable registration guide blank against the adjustable model to create a custom registration guide based on the adjustable model which is based on the patient's bone. As described above, the outer surface 22 of the adjustable model 18, as shown in FIG. 5, has been manipulated to create a three-dimensional model of the patient's bone. The malleable registration guide blank 24, may be placed onto the outer surface 22 of the adjustable model. The blank 24 may be pressed, hammered, or molded onto the outer surface of the adjustable model. For example, the malleable registration guide blank 24 may be a thin malleable sheet of material. For example, the blank may be made of any suitable malleable metal, polymer, or plastic. Preferably, the material is configured to be hammered or pressed permanently into shape without breaking or cracking. In other words, the blank 24 preferable holds the shape of the three-dimensional model once it is shaped against the model. In some embodiments, the material may melted or warmed before it is placed onto the model such that it will conform to the model and then cool to hold its shape. In some embodiments, the model may further include vacuum or suction such that the blank 24 may be pulled against the model and shaped. In some embodiments, the malleable material may be heated or cured to increase its material stiffness once it has been shaped against the model. The malleable registration guide blank 24 may alternatively be shaped against the model in any other suitable fashion.

In specific embodiments, the method 200 may further include the step of sterilizing the registration guide. In some embodiments, the adjustable model (at least the distal ends of the moveable elements) and the malleable registration blank may be sterile, and the blank may be shaped in a sterile environment. The registration guide is preferably sterilized prior to coupling the registration guide to the bone.

As shown in FIG. 2, the method 200 may include block S230, which recites coupling the shaped registration guide and fiducial markers to the patient's bone. Block S230 preferably functions to couple the custom registration guide to the patient's bone. The custom registration guide is shaped such that it fits with the patient's bone in a unique way. The fiducial markers may be a part of the registration guide, or they may be separate modular pieces that attach in a specific location or through an opening in the guide. As described above, the fiducial markers may be features shaped into the registration guide that are not present in the patient's bone, but that can be used to rapidly determine the spatial location and orientation of the registration guide. For example, the registration guide may include holes or divots in specific locations that may function as fiducial markers or may provide a location through which a fiducial marker may be coupled to the registration guide and/or to the bone. In certain embodiments, the fiducial markers may be optical, mechanical, electro-magnetic, or any other suitable fiducial markers.

As shown in FIG. 2, the method 200 may include block S240, which recites immobilizing the registration guide with respect to the bone. Block S240 preferably functions to fix the custom registration guide to the patient's bone. For example, during the surgery, once the registration guide is applied to the bone intraoperatively, the guide can be secured to the bone using fixation pins, fasteners, or another method of immobilizing the guide with respect to the bone. The fixation pins may or may not also serve as the fiducial markers.

As shown in FIG. 3, a method 300 for intraoperatively determining the location of a patient's bone may include the steps of determining intraoperatively the location of the fiducial markers in block S310; determining the location of the registration guide with respect to the fiducial markers in block S320; and determining the location of the patient's bone with respect to the registration guide in block S330. In some embodiments, the method 300 for intraoperatively determining the location of a patient's bone may further include the step of performing a surgical procedure on the patient's bone in block S340. The method 300 preferably functions to precisely locate the position of a patient's bone in three-dimensional space to enable a surgical procedure to be performed on the bone in its known location. For example, this may be particularly useful in robotic-assisted or computer-assisted surgery (e.g., computer navigation). For example, in a joint arthroplasty procedure in the orthopedic surgery field, accurate placement and alignment of an implant is a large factor in determining the success of the procedure. A slight misalignment may result in poor wear characteristics, reduced functionality, and a decreased longevity. Knowing the exact location of the bone in three-dimensional space prior to making any bone cuts enables accurate implant placement and alignment.

As shown in FIG. 3, the method 300 may include block S310, which recites determining intraoperatively the location of the fiducial markers. Block S310 functions to find, in three-dimensional space, the location of the fiducial markers of the registration guide or coupled to the registration guide and/or bone. In some embodiments, the locations of the fiducial markers may be determined using a digitizer or other locating device.

As shown in FIG. 3, the method 300 may include blocks S320 and S330, which recite determining the location of the registration guide with respect to the fiducial markers and determining the location of the patient's bone with respect to the registration guide. Blocks S320 and S330 function to determine the location of the registration guide with respect to the fiducial markers based on the known spatial relationship between the fiducial markers and the registration guide, and to determine the location of the patient's bone with respect to the registration guide based on the unique fit and known spatial relationship between the registration guide and the patient's bone. Once the location of the fiducial markers has been determined, the location and orientation of the underlying bone can be determined as there is a unique mating between the registration guide and the bone, and the position of the fiducial markers with respect to the registration guide is known by the design of the registration guide.

As shown in FIG. 3, the method 300 may include block S340, which recites performing a surgical procedure on the patient's bone. Block S340 functions to perform a surgical procedure on the patient's bone while knowing the precise location of the patient's bone in three-dimensional space. For example, a joint arthroplasty procedure in the orthopedic surgery field may be performed knowing the exact location of the bone in three-dimensional space prior to making any bone cuts, thereby enabling accurate implant placement and alignment and improved likelihood of success of the procedure. Another example, an osteotomy procedure in the orthopedic surgery field may be performed knowing the orientation of the bone in three-dimensional space prior to making the bone cuts to increase the accuracy of making the bone cuts as desired. In some embodiments, prior to beginning the bone cutting, the registration guide may or may not be removed from the bone surface. If the registration guide is removed from the surface of the bone, the fiducial markers remain attached to the bone during bone cutting. These fiducial markers can be used at any point during the surgery to rapidly determine the location and orientation of the bone.

FIG. 4 illustrates an embodiment of a system for creating a three-dimensional model of a patient's bone that includes a processor 10 configured to receive patient scan data 12 and to transform the patient scan data into adjustable model instructions 14; a machine 16, coupled to an adjustable model 18 having a plurality of moveable elements 20, configured to receive the adjustable model instructions and to move a number of the moveable elements 20. In certain embodiments, the processor 10 may be further configured to transform the patient scan data 12 into a three-dimensional virtual model, and the adjustable model instructions 14 may be developed based on the virtual three-dimensional model.

In specific embodiments, the processor 10 may be coupled to the machine 16. The system preferably functions to create a three-dimensional model of a patient's bone based on the patient scan data input 12. The system preferably functions to create a three-dimensional model of a patient's bone in sufficient detail that a custom registration guide may be shaped by the three-dimensional model. In some embodiments, the system preferably functions to create features or other markers in the three-dimensional model that may be transferred to the registration guide to aid in the bone registration process. In specific embodiments, the system preferably functions to enable the fabrication or creation of the three-dimensional model locally, for example, at the bedside or within the hospital, rather than having to send out the patient information and receive the three-dimensional model from a third party, thus reducing time, cost, and potential for error. The system is preferably used for bone registration for orthopedic surgery, but may alternatively be used for any suitable applications, clinical or otherwise.

As shown in FIG. 4, the processor 10 is configured to receive patient scan data 12 and to transform the patient scan data into adjustable model instructions 14. The processor 10 preferably functions to create instructions for the creation of a physical three-dimensional surface model based on the patient scan data. In certain embodiments, the processor 10 may run preoperative surgical planning software. In some embodiments, the scan data 12 may be in the form of CT, MRI, or X-ray scans of patients' bones. The scan data 12 may be collected by the systems and methods described herein or may alternatively, be collected prior to the creation of the custom registration guide by systems and methods specific to imaging.

Continuing with FIG. 4, the machine 16 is configured to receive the adjustable model instructions and to move a number of the moveable elements 20 of the adjustable model 18. The machine 16 preferably functions to create the physical three-dimensional model based on the patient scan data and/or a virtual three-dimensional model. The machine 16 is preferably coupled to the proximal ends of each of the moveable elements 20. In some embodiments, the machine 16 is coupled to the processor 10. In some alternative embodiments, the machine may be separate from the processor 10 and the instructions 14 from the processor may be entered into the machine 16. In some embodiments, the moveable elements may be moved manually based on the instructions rather than using a machine 16.

As shown in FIGS. 4 and 5, the adjustable model 18 may include a plurality of moveable elements 20. In specific embodiments, the adjustable model 18 may further include an adjustable outer surface 22 coupled to the distal end of the plurality of moveable elements 20. As described above in reference to FIG. 4, in some embodiments, the proximal ends of the moveable elements 20 are each coupled to a robot or machine 16 capable of carrying out a series of actions automatically. Based on a set of instructions 14, the machine 16 may move a number of the moveable elements 20 to a specific location such that the adjustable model takes on a specific shape. Alternatively, the number of moveable elements may be moved manually based on a set of instructions.

As shown in FIG. 5, the adjustable model 18 may include a plurality of moveable elements 20 that are configured to move into position such that the outer surface 22 of the model takes on the shape of the three dimensional model of the patient's bone. In some embodiments, the outer surface 22 may comprise a membrane or substrate coupled to the distal ends of the moveable elements 20. The membrane preferably functions to smooth the surface, such that it is one continuous surface rather than a plurality of discrete points in specific locations. In some embodiments, the membrane may better allow the adjustable model to mimic the actual geometries and anatomical features of the patient's bone. In some embodiments, the model 18 may further include a locking mechanism to fix the moveable elements into position once they have been moved to create the three dimensional model of the patient's bone.

In one embodiment, the plurality of moveable elements 20 may be a plurality of moveable pins. The proximal ends of the pins may be moved up or down such that the distal ends of the pins form an outer surface that takes on the desired shape of the three-dimensional model of the patient's bone. In some embodiments, the resolution of the three-dimensional model may be determined by the number of pins, and/or the spacing between the pins. In certain embodiments, each pin may be directly adjacent to its neighboring pins such that there is essentially no space between in the pins. In some embodiments, the distance from pin to pin (and/or the diameter of a pin) may be between 0 mm and 1 mm, while in some embodiments, the distance from pin to pin (and/or the diameter of a pin) may be between 0 mm and 2.5 mm. In some embodiments, the distance from pin to pin (and/or the diameter of a pin) may be between 0 mm and 5 mm. The spacing and sizing of the pins is preferably configured to enable a high resolution of the three dimensional model such that the detailed model may enable the creation of a detailed registration guide that uniquely couples to the patient's bone.

Figure 7A:
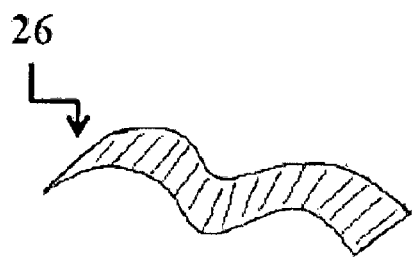
FIGS. 7A and 7B illustrates exemplary malleable registration guides in a shaped configuration in accordance with embodiments of the invention.
Figure 7B:
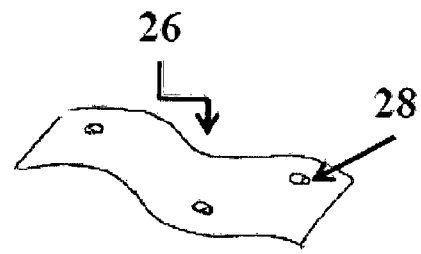

As shown in FIGS. 6-7B, a system for creating a custom registration guide preferably includes a malleable registration guide blank 24 and an adjustable model 18 (as shown in FIG. 5). The malleable registration guide blank 24 is placed onto the adjustable model 18 and shaped to fit the adjustable model 18, thus creating custom registration guide 26. The system preferably functions to create a custom registration guide 26 that fits to the patient's bone in a unique way. In certain embodiments, the system preferably functions to enable the fabrication or creation of the custom registration guide locally, for example, at the bedside or within the hospital, rather than having to send out the patient information and receive the custom registration guide from a third party, thus reducing time, cost, and potential for error. In some embodiments, the method system functions to enable the fabrication or creation of the custom registration guide manually and/or requiring minimal use of tools.

Continuing with FIG. 6, the malleable registration guide blank 24 is preferably configured to conform to the shape of the adjustable model 18. The blank 24 may be pressed, hammered, or molded onto the outer surface of the adjustable model. For example, the malleable registration guide blank 24 may be a thin malleable sheet of material. For example, the blank 24 may be made of any suitable malleable metal or plastic. The material of the registration guide is preferable sterile and/or sterilizable, and the material may be hammered or pressed permanently into shape without breaking or cracking. In other words, the blank 24 preferable holds the shape of the three dimensional model once it is shaped against the model. In certain embodiments, the material for the blank 24 may melted or warmed before it is placed onto the model such that it will conform to the model and then cool to hold its shape. In some embodiments, the model may further include vacuum or suction such that the blank 24 may be pulled against the model and shaped. In some embodiments, the malleable material may be heated or cured to increase its material stiffness once it has been shaped against the model. The malleable registration guide blank 24 may alternatively be shaped against the model in any other suitable fashion.

In certain embodiments, the registration guide may be modular in nature, consisting of multiple pieces. The pieces of the registration guide 26 may each be shaped against the model. In some embodiments, the pieces of the registration guide 26 may be fixed or coupled together and then configured to break apart. For example, once the registration guide 26 is secured to the bone, part of the registration guide can be removed from the bone, leaving part of the guide fixed to the bone. The part that remains fixed to the bone preferably contains on or within it, fiducial markers that may be used to determine the location and orientation of the registration guide 26. Once the location and orientation of these fiducial markers is known, the original location of the registration guide can be determined and the location and orientation of the underlying bone can be determined as there is a unique mating between the bone and the registration guide 26.

As shown in FIGS. 7A and 7B the shaped custom registration guide 26 is preferably configured to fit to the patient's bone in a unique way. As shown, the shaped registration guide 26 holds the shape received from the model. The registration guide 26 includes an anatomy-specific inner surface that mates with the bone surface in a unique manner and an external surface, as shown in FIG. 7B, including fiducial markers 28 or distinguishing features that can be used to determine the location of the registration guide. The fiducial makers 28 may be optical, mechanical, electromagnetic, or any other suitable markers. The fiducial markers 28 may be a part of the registration guide, or the fiducial markers 28 may be separate modular pieces that attach in a specific location or through an opening in the guide 26. The fiducial markers 28, whose positions relative to the registration guide 26 are known, and whose positions relative to the patient bone will be known once the registration guide 26 is placed on the bone in its unique position, can then be rapidly located intraoperatively to determine the spatial orientation of the bone in three-dimensions. The registration guide 26 and/or fiducial markers 28 may or may not be removed from the patient bone prior to cutting of the bone surface.

In one specific embodiment, the patient's bone may include a proximal tibia. The custom registration guide 26 may be created such that it conforms to the surface of the bone, and reaches over at least three of the four sides of the tibial plateau (anterior, posterior, medial, and lateral), thus ensuring that the guide 26 will fit on the bone in a unique manner. In another specific embodiment, the patient's bone may include the distal femur. The custom registration guide 26 may be created such that it conforms and mates with the femoral joint surface of the patient and nests within the femoral intercondylar notch. In a third specific embodiment, the patient's bone includes the proximal femur for a total hip arthroplasty procedure. The custom registration guide 26 may be created such that it conforms and mates with the femoral joint surface of the patient. The custom registration guide 26 may fit in a conforming manner on the surface of the femoral head and neck in a unique position.

Figure 8:
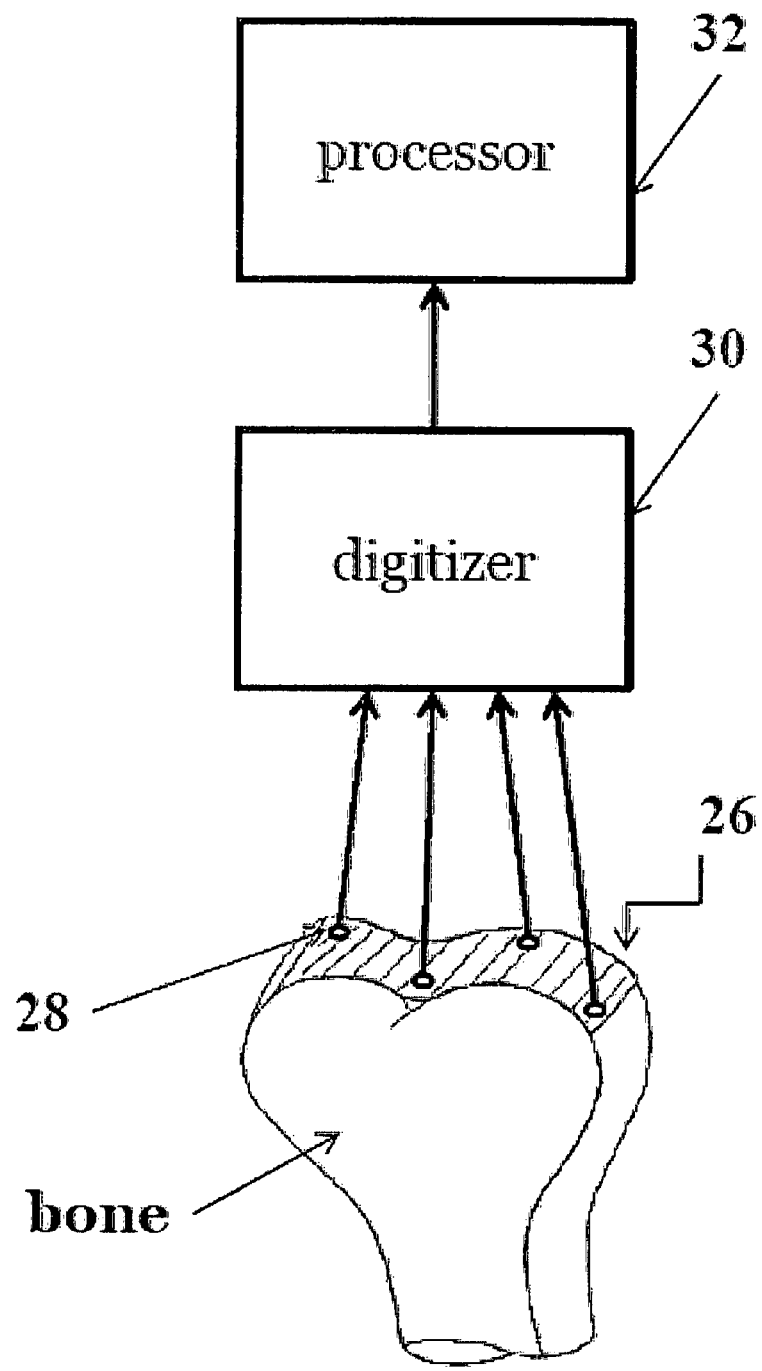
FIG. 8 illustrates an exemplary malleable registration guide in a shaped configuration, as shown in FIG. 7A, fixed to the exemplary patient bone as shown in FIG. 4 according to an embodiment of the invention.

As shown in FIG. 8, an embodiment of a system for intraoperatively determining the location of a patient's bone includes a custom registration guide 26, a digitizer 30 configured to determine intraoperatively the location of the fiducial markers 28; and a processor 32, coupled to the digitizer 30, and configured to determine the location of the registration guide with respect to the fiducial markers and to determine the location of the patient's bone with respect to the registration guide. The system preferably functions to precisely locate the position of a patient's bone in three-dimensional space to enable a surgical procedure to be performed on the bone in its known location. For example, this may be particularly useful in robotic-assisted or computer-assisted surgery (e.g., computer navigation). For example, in joint arthroplasty procedure in the orthopedic surgery field, accurate placement and alignment of an implant is a large factor in determining the success of the procedure. A slight misalignment may result in poor wear characteristics, reduced functionality, and a decreased longevity. Knowing the exact location of the bone in three-dimensional space prior to making any bone cuts enables accurate implant placement and alignment.

As shown in FIG. 8, the custom registration guide 26 is coupled to the patient's bone. In certain embodiments, the guide 26 is fixed or immobilized with respect to the patient's bone. As described in detail above, the digitizer 30 preferably functions to determine intraoperatively the location of the fiducial markers 28. Once the location of the fiducial markers is known, the processor 32 preferably functions to determine the location of the registration guide 26 with respect to the fiducial markers 28, and to determine the location of the patient's bone with respect to the registration guide 26.

The processor 32 preferably functions to determine the location of the registration guide 26 with respect to the fiducial markers 28 based on the known spatial relationship between the fiducial markers 28 and the registration guide 26, and to determine the location of the patient's bone with respect to the registration guide 26 based on the unique fit and known spatial relationship between the registration guide 26 and the patient's bone. Once the location of the fiducial markers 28 has been determined, the location and orientation of the underlying bone can be determined, as there is a unique mating between the registration guide 26 and the bone, and the position of the fiducial markers 28 with respect to the registration guide 26 is known by the design of the registration guide 26.

Figure 9:
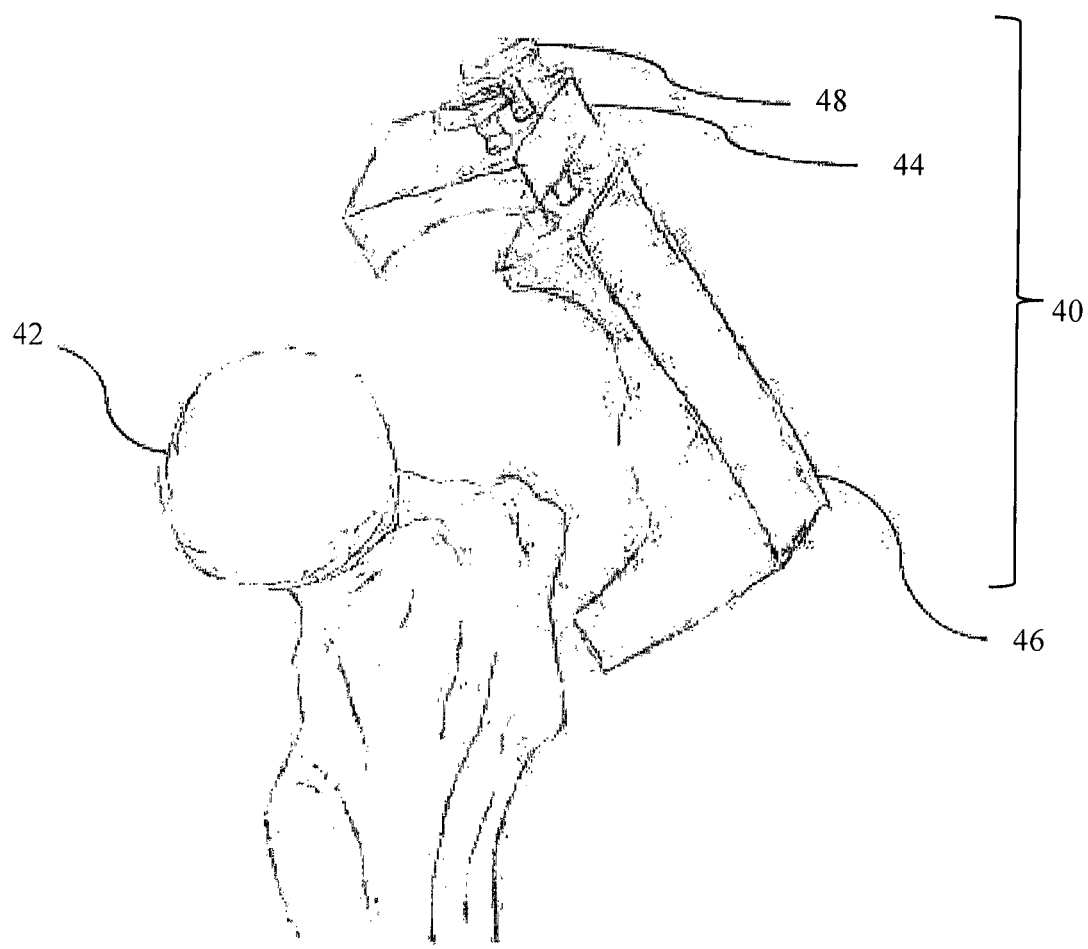
FIG. 9 is a perspective view of a proximal femur with an embodiment of the adjustable registration jig in position on the bone.

FIG. 9 is a perspective view of a proximal femur 42 with an embodiment of the adjustable registration jig 40. The jig 40 is made of two separate upper 44 and lower 46 parts that conform exactly to the surface of the bone and can be adjusted using a mechanism 48, which ensures that the guide fits on the bone 42 securely in a unique manner.

Figure 10:
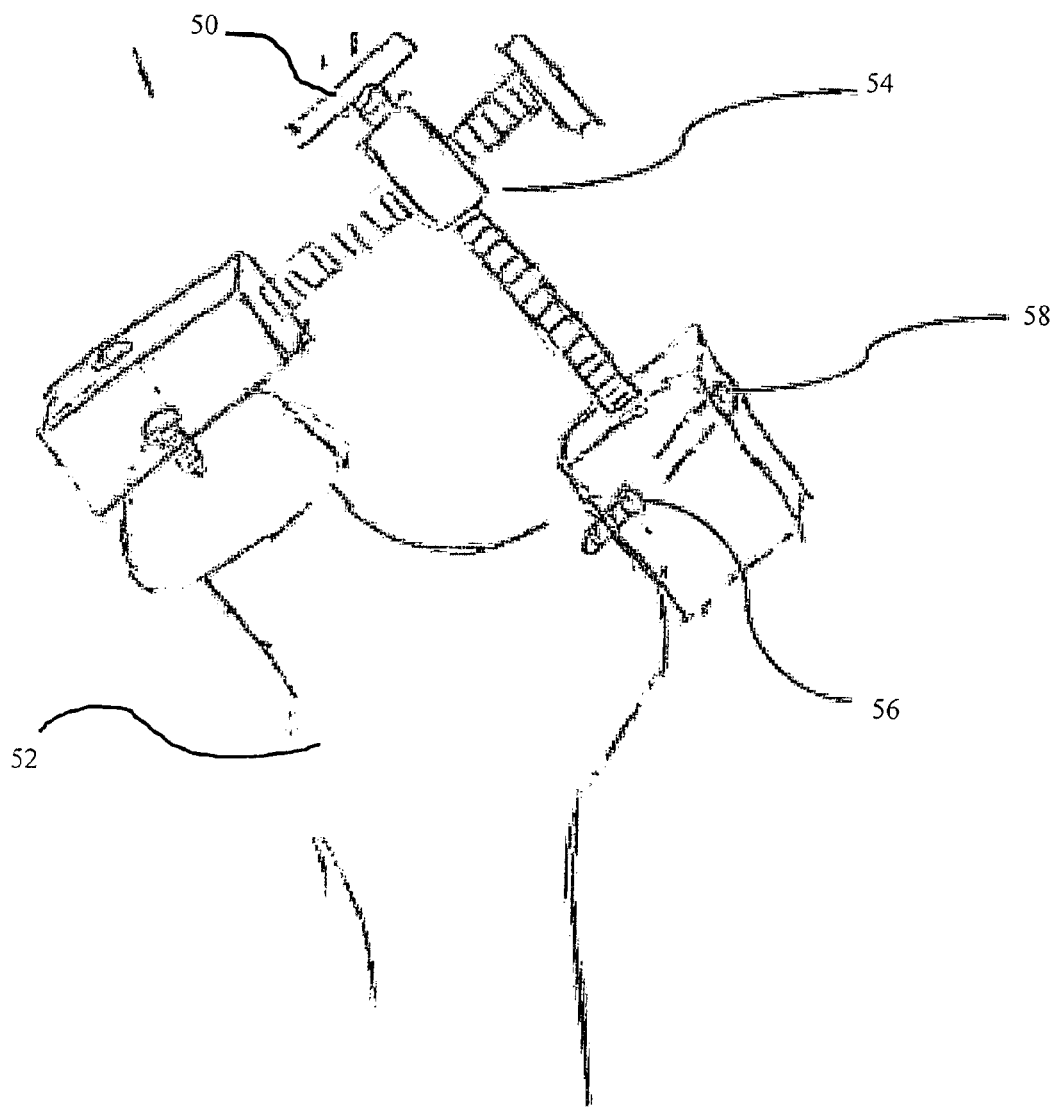
FIG. 10 is a perspective view of the proximal tibia with an embodiment of the adjustable registration jig in position on the bone.

FIG. 10 is a perspective view of the proximal tibia 52 with an embodiment of a generic adjustable registration jig 50 in position on the bone 52. The jig 50 can be adjusted using a mechanism 54. Once the jig 50 is placed on the bone 52, fiducial markers 56 can be placed into the bone 52 through an opening shown by reference numeral 58. Once the fiducial markers 56 have been placed in the bone 52, the registration jig 50 may be removed prior to bone cutting.

Figure 11:
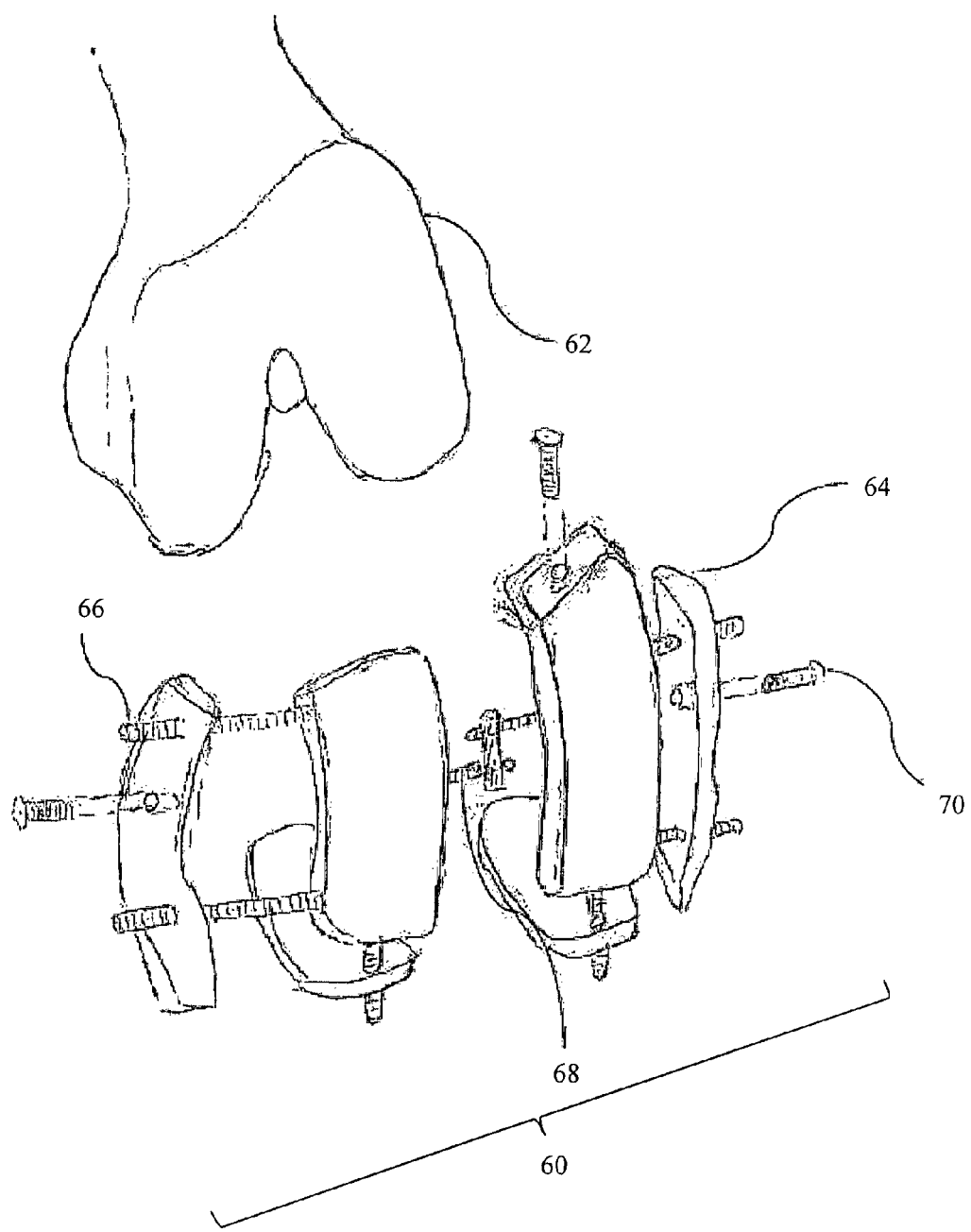
FIG. 11 is a perspective view of a distal femur with an embodiment of the adjustable registration jig shown next to the bone.

FIG. 11 is a perspective view of a distal femur 62 with an embodiment of a generic adjustable registration jig 60 shown next to the bone.

The adjustable jig 60 consists of multiple pieces such as 64 that can be adjusted using mechanisms, such as those represented by reference numerals 66 and 68 to secure it to the surface of the bone. Once the jig has been adjusted according to the settings provided by the preoperative planning software, fiducial markers, such as 70, can be placed through openings in the jig 60 and secured to the bone 62. These fiducial markers 70 can be used to determine the location and orientation of the bone 62 based on the preoperative planning software.

Figure 12C:
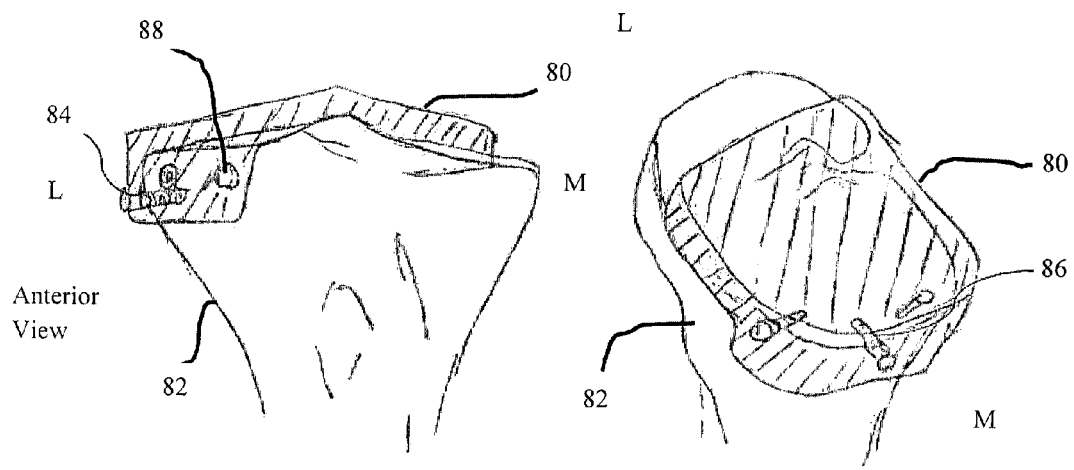
Figure 12C:
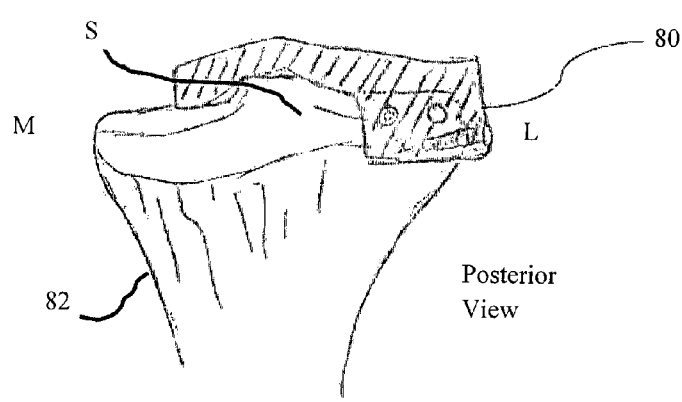

FIGS. 12A-12C are three perspective views of an embodiment of the inventive registration guide as applied to a proximal tibia. The guide 80 conforms exactly to the surface S of the bone 82 and reaches over at least three of the four sides of the tibial plateau (anterior, posterior, medial, and lateral) to ensure that the guide will fit on the bone in a unique manner. Once the guide 80 is placed on the bone 82, fiducial markers such as 84 and 86 amongst others shown may be secured into the bone 82 through holes 88 within the guide 80.

Figure 13A:
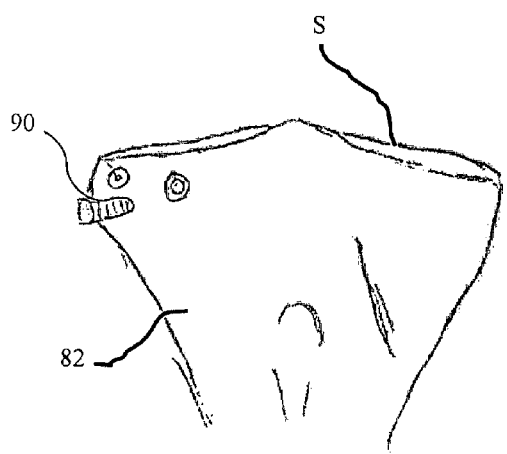
FIGS. 13A-13C are skeletal representations of the proximal human tibia from various perspectives demonstrating how the fiducial markers would remain on the bone when the registration guide is removed according to embodiments of the invention.
Figure 13B:
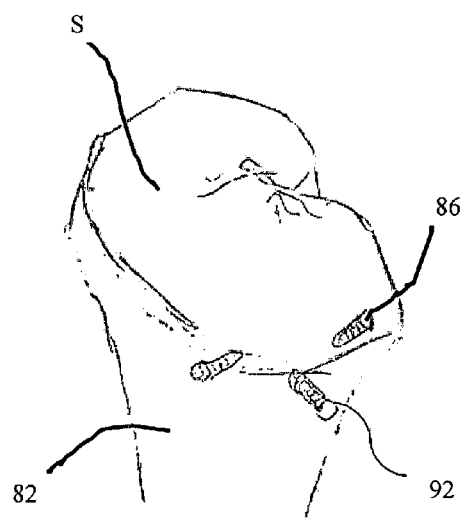
Figure 13C:
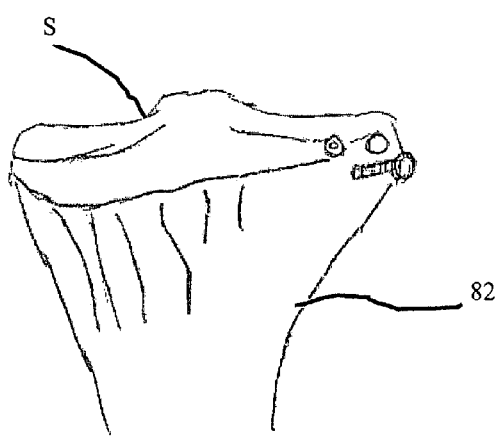

FIGS. 13A-13C are perspective views of the proximal tibia bone 82 after the registration guide 80 has been removed from the bone 82, but the fiducial markers have been left in the bone. These fiducial markers, represented by 90 and 92, are in specific locations within the bone 82 as determined by the registration guide 80, and marker locations in space can be used to orient the bone 80 in three dimensions.

Figures 14A, 14B:
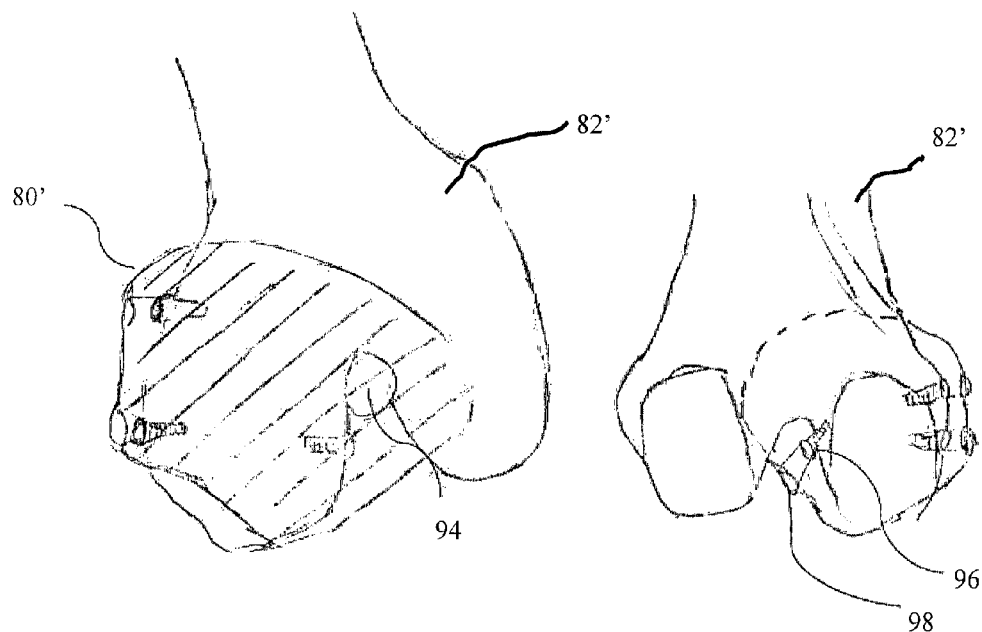
FIGS. 14A-14B are skeletal representations of the distal human femur from various perspectives demonstrating how the registration guide would fit on the bone according to embodiments of the invention.

FIGS. 14A and 14B are perspective views of an embodiment of the inventive guide applied to the distal femur 82'. The registration guide 80' includes an inner guide surface designed to closely conform and mate with the femoral joint surface S' of the patient in three-dimensional space such that the registration guide 80' and the femoral joint surface S' nests within the femoral intercondylar notch 94. As such, the registration guide 80' will fit in a conforming manner on the surface S' of the femur 82' in a unique position as determined by the preoperative planning software. Fiducial markers such as 96 can then be placed through holes such as 98 in the registration guide 80' and secured to the bone 82'.

Figures 15A, 15B:
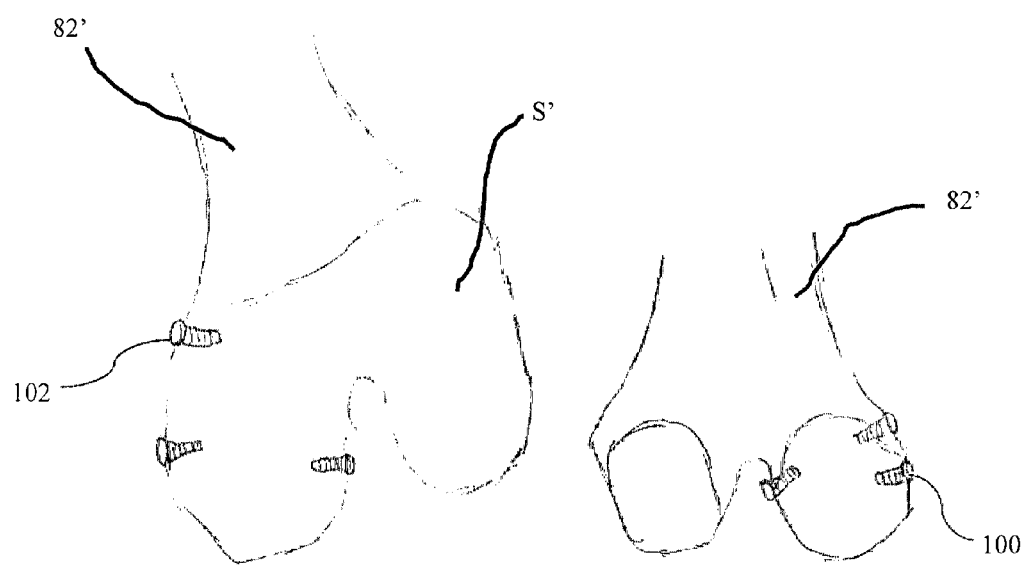
FIGS. 15A-15B are skeletal representations of the distal human femur from various perspectives demonstrating how the fiducial markers would remain on the bone when the registration guide is removed according to embodiments of the invention.

FIGS. 15A and 15B show two views of the distal femur after the registration guide 80' has been removed from the bone 82', but the fiducial markers have been left in the bone 82'. These fiducial markers 100 and 102 are in specific locations within the bone 82' as determined by the registration guide 80' and their locations in space can be used to orient the bone 82' in three dimensions. Three or more fiducial markers should remain within the bone for orientation purposes.

Figures 16A, 16B:
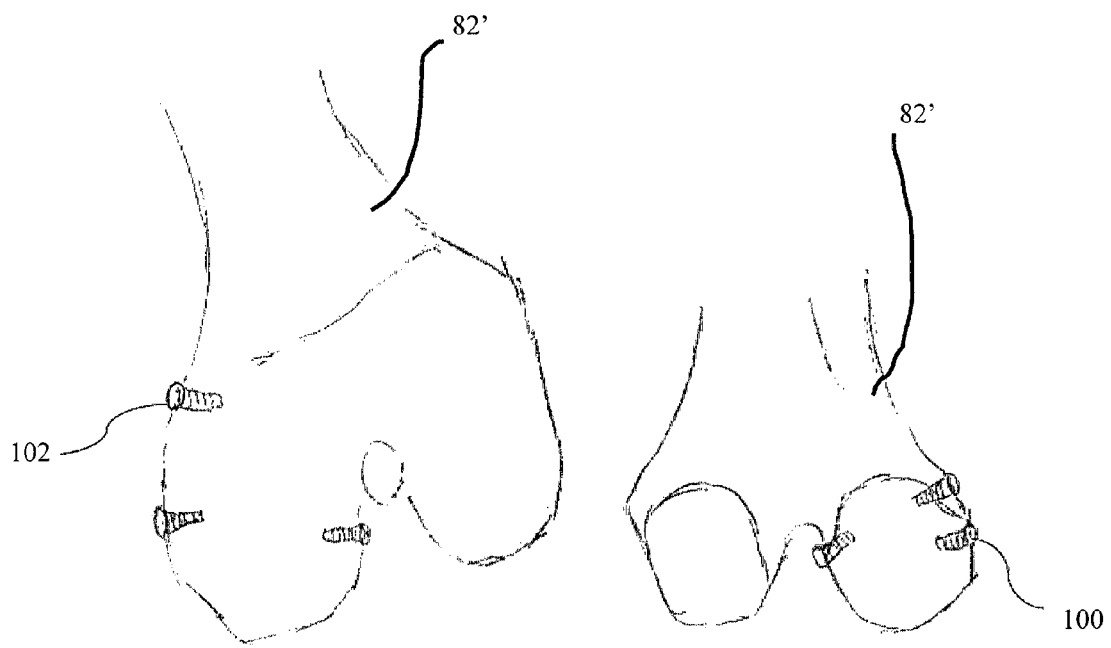
FIGS. 16A and 16B shows two views of an embodiment of the invention applied to the proximal femur for a total hip arthroplasty procedure.

FIGS. 16A and 16B shows two views of an embodiment of the invention applied to the proximal femur 82' for a total hip arthroplasty procedure. The registration guide 80' includes an inner guide surface designed to closely conform and mate with the femoral joint surface S' of the patient in three-dimensional space. The registration guide 80' will fit in a conforming manner on the surface S' of the femoral head and neck in a unique position as determined by the preoperative planning software. Fiducial markers 100 and 102 can then be placed through holes in the registration guide 80' and secured to the bone.

As a person skilled in the art will recognize from the previous detailed description and from the figures and claims, modifications and changes can be made to the preferred embodiments of the invention without departing from the scope of this invention defined in the following claims.

The invention claimed is:

1. A method for creating a three-dimensional surface model of a bone of a patient for registering a position and orientation of the bone, the method comprising:
   receiving scan data of the bone of the patient;
   creating instructions based on the scan data;
   moving a plurality of moveable elements, coupled to an adjustable model, based on the instructions for creating the three-dimensional surface model of the bone of the patient;
   coupling a malleable registration guide blank to the adjustable model to create a custom registration guide resembling the three-dimensional surface model of the bone; and
   registering the position and orientation of the bone of the patient to a computer-assisted device by assembling the custom registration guide to a matching surface on the bone of the patient.

2. The method of claim 1, further comprising: creating a virtual three-dimensional model for creating the instructions for creating the three-dimensional surface model of the bone of the patient.

3. The method of claim 2, wherein creating instructions further comprises creating instructions based on the virtual three-dimensional model of the bone of the patient for creating the three-dimensional surface model of the bone of the patient.

4. The method of claim 1, further comprising locking the moveable elements into position.

\* \* \* \* \*

UNITED STATES PATENT AND TRADEMARK OFFICE
CERTIFICATE OF CORRECTION

PATENT NO. : 10,002,227 B2
APPLICATION NO. : 14/429301
DATED : June 19, 2018
INVENTOR(S) : Nathan A. Netravali, In K. Mun and Lu Li Page 1 of 1

It is certified that error appears in the above-identified patent and that said Letters Patent is hereby corrected as shown below:

On the Title Page

In the Inventors: section, please delete "Li Lu, Sunnyvale, CA (US)" and replace with "Lu Li, Sunnyvale, CA (US)"

Signed and Sealed this
First Day of January, 2019

Andrei Iancu
*Director of the United States Patent and Trademark Office*